United States Patent [19]
Lau et al.

[11] Patent Number: 5,270,453
[45] Date of Patent: Dec. 14, 1993

[54] AROMATIC BISTRIAZENE COMPOUNDS

[75] Inventors: Aldrich N. K. Lau, Palo Alto; Lanchi P. Vo, San Jose; Frank W. Mercer, Belmont, all of Calif.

[73] Assignee: Raychem Corporation, Menlo Park, Calif.

[21] Appl. No.: 977,472

[22] Filed: Nov. 17, 1992

Related U.S. Application Data

[60] Division of Ser. No. 583,898, Sep. 17, 1990, Pat. No. 5,173,542, which is a continuation-in-part of Ser. No. 447,750, Dec. 8, 1989, abandoned.

[51] Int. Cl.$^5$ .......................... C07C 245/24
[52] U.S. Cl. .......................... 534/550; 534/555; 534/554
[58] Field of Search .......................... 534/550, 554

[56] References Cited

U.S. PATENT DOCUMENTS

| | | | |
|---|---|---|---|
| 3,138,521 | 6/1964 | Jelinek et al. | 430/196 X |
| 3,555,004 | 1/1972 | Mueller et al. | 260/181 |
| 4,565,767 | 1/1986 | Kataoka et al. | 430/196 |
| 4,656,115 | 4/1987 | Arfai et al. | 430/196 X |
| 4,656,116 | 4/1987 | Rohde et al. | 430/197 |
| 4,732,843 | 3/1988 | Budde et al. | 430/312 |
| 4,744,007 | 5/1988 | Watari et al. | 361/386 |
| 4,835,197 | 5/1989 | Mercer et al. | 430/312 X |
| 5,144,780 | 5/1992 | Mercer et al. | 430/312 X |
| 5,155,175 | 1/1992 | Mercer et al. | 430/312 X |

FOREIGN PATENT DOCUMENTS

| | | | |
|---|---|---|---|
| 0736959 | 8/1969 | Belgium | 430/196 X |
| 1282757 | 7/1972 | United Kingdom | 107/6 |

OTHER PUBLICATIONS

Pochinok et al, Ukr. Khim. Zhurnal, vol. 25(6), pp. 774–780 (1959).

(List continued on next page.)

*Primary Examiner*—Floyd D. Higel
*Attorney, Agent, or Firm*—Herbert G. Burkard; Yuan Chao

[57] ABSTRACT

Aromatic bistriazene compounds of the formula $$\begin{array}{c} R_1 \\ \diagdown \\ N-N=N-\text{Ar}-R_5-\text{Ar}-N=N-N \diagup \begin{array}{c} R_3 \\ \diagdown \\ R_4 \end{array} \\ R_2 \diagup \end{array}$$

wherein —$R_1$, —$R_2$, —$R_3$, and —$R_4$ are independently —H, —$C_6H_5$, —$C_6H_4Y$, or $C_1$-$C_4$ alkyl; —$R_5$— is —O—(phenyl)—(phenyl)—O—, —O—(phenyl)—C($CF_3$)($CF_3$)—(phenyl)—O—, —O—(phenyl)—O—(phenyl)—O—, fluorene group, —O—(phenyl with $(R_6)_r$ and $F_{4-r}$)—(phenyl with $(R_6)_r$ and $F_{4-r}$)—O—, or —O—(phenyl with $(R_6)_r$ and $F_{4-r}$)—O—;

—$R_6$ is —F, —Cl, —Br, —$CH_3$, or —$CF_3$; $r$ is 0, 1, 2, 3, or 4; and —Y is halogen, —$NO_2$, —$C_6H_5$, or $C_1$-$C_4$ alkyl. These bistriazene compounds are useful for crosslinking polymers such as poly(imides), poly(aryl ether ketones), poly(aryl ether sulfones), poly(quinolines), poly(quinoxalines), and nonaromatic fluoropolymers having aliphatic C—H groups.

10 Claims, No Drawings

OTHER PUBLICATIONS

Mazza et al., II Farmaco Ed. Sc., 29, pp. 58–72 (1974).
"Microelectronics Packaging Handbook," Tummala et al.(eds.), pp. 687–692 (van Nostrand Reinhold 1989).
Stille, Macromolecules 14, 870 (1981).
Norris et al., Macromolecules 9, 496 (1976).
Labadie et al., Sampe J. 25(6), 18 (1989).
Hergenrother, J. Macromol. Sci. Rev. Macromol. Chem. C6(1), 1 (1971).
Chem. Abs. 89:60506a (1978).
Chem Abs. 89:6837 (1978).
Chem. Abs. 69:97551v (1968).
Burkey et al., J. Org. Chem. 48, 3704 (1983).
Vernin et al., J. Org. Chem. 48, 3704 (1983).
Vernin et al., J. Heterocycl. Chem. 46, 97 (1979).
Vernin et al., J. Chem. Research (S) 151 (1980).
Vernin et al., J. Chem. Research (S) 26 (1979).
Vernin et al., (12) 921 (1978).
Buxton et al., J.C.S. Chem. Comm. 545 (1973).
Elks et al., J. Chem. Soc. 441 (1943).
Rondestvedt et al., J. Amer. Chem Soc. 77, 1769 (1955).
Smith, Jr., et al., J. Org. Chem. 53, 1467 (1988).
Takeishi et al., Polymer Letters 8, 829 (1970).
Patent Abstracts of Japan, vol. 10, No. 172 (C-354)(2228), Jun. 18, 1986 (abstract of JP 61-021,131, Mitsubishi Denki).
Derwent WPI Abstract No. 78-90377A [50] (Abstract of JP 53-127723 (Hitachi).

AROMATIC BISTRIAZENE COMPOUNDS

CROSS-REFERENCE to RELATED APPLICATIONS

This application is a divisional of application Ser. No. 07/583,898, filed Sep. 17, 1990, now U.S. Pat. No. 5,173,542, which is a continuation-in-part of application Ser. No. 07/447,750, filed Dec. 8, 1989, now abandoned, the disclosures of which are incorporated herein by reference.

BACKGROUND OF THE INVENTION

This invention relates to novel bistriazene compounds, crosslinkable and crosslinked polymer compositions made with the same, and multilayer electronic circuit articles having polymers crosslinked with bistriazene compounds as an interlayer insulating material.

Aromatic polymers have properties such as superior mechanical strength, thermal stability, and solvent resistance, which make them valuable in a wide variety of applications. The term "aromatic polymer" means herein a polymer which has aromatic groups incorporated into its backbone. Among the better known aromatic polymers are poly(imides), poly(aryl ether sulfones), and poly(aryl ether ketones). Aromatic polymers can be used in diverse applications, such as adhesives, coatings, matrix resins for fiber reinforced composite structures, and molded or extruded articles. They are also used as insulators in various electronic applications, such as in multilayer integrated circuit articles.

Fluorinated polymers are also desirable polymers, generally possessing superior thermal stability and solvent resistance. Among the better known fluorinated polymers are poly(tetrafluoroethylene) (PTFE), poly(vinylidene fluoride), poly(vinyl fluoride), and ethylenetetrafluoroethylene copolymer (ETFE). Fluorinated polymers have many uses, such as insulation, molded articles, coatings, and films.

Despite their generally superior properties, it is often desirable to enhance or improve the thermal and/or solvent resistance properties of aromatic or fluorinated polymers. For example, some aromatic polymers are susceptible to solvent-induced stress cracking. Or, there may be a decrease in the mechanical properties as a polymer is heated up to or past a transition temperature (such as the glass transition temperature $T_g$ or the crystalline melting temperature $T_m$).

When crosslinking a polymer, the crosslinking reaction should be readily controlled—it should not be prematurely triggered (for example before the polymer has been formed into its final shape), but at the same time it should be conveniently initiated at the desired moment. Nor should the crosslinking process cause degradation of the polymer. The crosslinks should not be weak links which are themselves subject to thermooxidative attack, nor introduce undesirable characteristics into the final composition, rendering it unsuitable for its intended end use (for example by making the composition more moisture absorbent when low moisture absorption is a critical performance parameter).

It is known to radiation crosslink polymers. Generally, radiation crosslinking occurs via free radicals formed by the scission of an aliphatic C—H bond. Aromatic polymers are difficult to radiation crosslink because aromatic C—H bonds are more stable than their aliphatic counterparts. Further, radiation crosslinking requires expensive equipment.

An alternative to radiation crosslinking is chemical crosslinking. It has been proposed to chemically crosslink aromatic polymers such as poly(imides) with acetylene, maleimide, or vinyl terminated compounds or oligomers in Mercer, U.S. Pat. No. 4,835,197 (1989). fluorinated polymers are difficult to crosslink chemically, because of their chemical inertness. Sometimes, a cure site monomer is copolymerized into a fluorinated polymer in order to provide it with crosslinking sites.

In view of the aforementioned considerations, it is desirable to develop crosslinking agents and methods which are conveniently controllable, wherein the crosslinking sites are stable, and which do not introduce undesirable functionalities into the polymeric composition being crosslinked. We have discovered novel crosslinking agents which achieve these objectives and which are especially effective for crosslinking aromatic or fluorinated polymers.

SUMMARY OF THE INVENTION

This invention provides a crosslinkable composition comprising (a) a polymer selected from the group consisting of poly(imide), poly(aryl ether ketone), poly(aryl ether sulfone), poly(quinoline), poly(quinoxaline), and nonaromatic fluoropolymer having aliphatic C—H groups and (b) a bistriazene compound of the formula

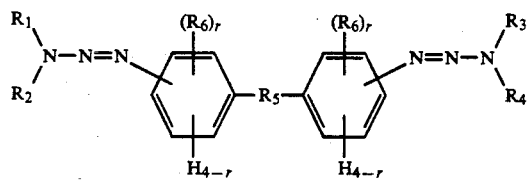

wherein —$R_1$, —$R_2$, —$R_3$, and —$R_4$ are independently —H, —$C_6H_5$, —$C_6H_5$, —$C_6H_4Y$, or $C_1$-$C_4$ alkyl; —$R_5$— is —O—, —$SO_2$—,

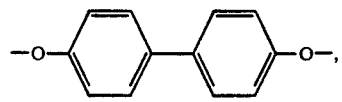

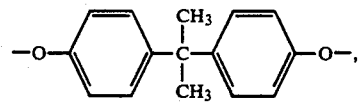

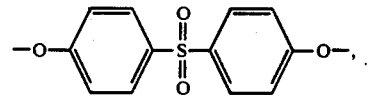

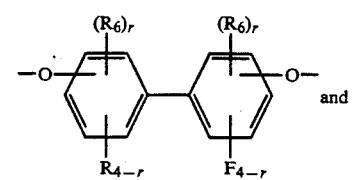

and

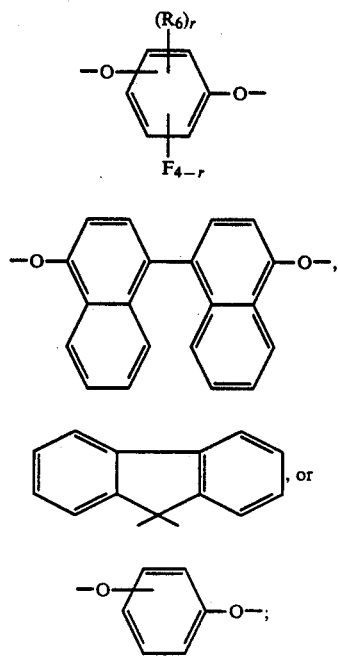

$R_6$ is —F, —Cl, —Br, —CH$_3$, or —CF$_3$; r is 0, 1, 2, 3, or 4; and —Y is halogen, —NO$_2$, —C$_6$H$_5$, or C$_1$-C$_4$ alkyl.

Preferably, each of —R$_1$, —R$_2$, —R$_3$ and —R$_4$ is methyl and r is 0. Also preferably, —R$_5$— is

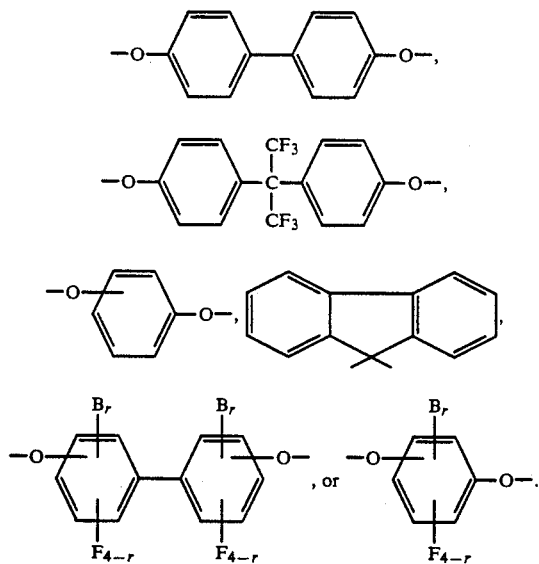

It is also preferred that the bistriazene groups be located para- to the —R$_5$— group.

Also provided is a crosslinked composition prepared from the aforementioned crosslinkable composition.

Our invention further provides a multilayer electronic circuit article comprising (a) a substrate; (b) a plurality of layers of an insulating material on a surface of the substrate; and (c) at least one layer of a conductive material interposed between two adjacent layers of the insulating material; the insulating material comprising a polymer crosslinked with the aforementioned bistriazene compounds.

DESCRIPTION OF THE PREFERRED EMBODIMENTS

The bistriazene compounds of this invention can be prepared by diazotizing a diamine precursor of the formula

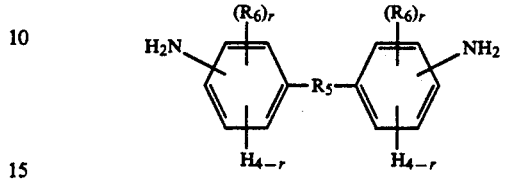

wherein —R$_5$—, R$_6$, and r are as defined hereinabove, in hydrochloric acid/sodium nitrite and then treating with an ammonia or an amine, for example dimethylamine.

The bistriazene compounds are particularly useful for crosslinking of aromatic polymers, which are difficult to crosslink by electron beam irradiation or with conventional crosslinking agents. Without being bound by theory, it is believed that, when heated up to or above a threshold temperature, the triazene groups decompose to form phenyl radicals. These then insert into aromatic groups in the polymer to form aryl-aryl crosslinkages, as illustrated by the following equations:

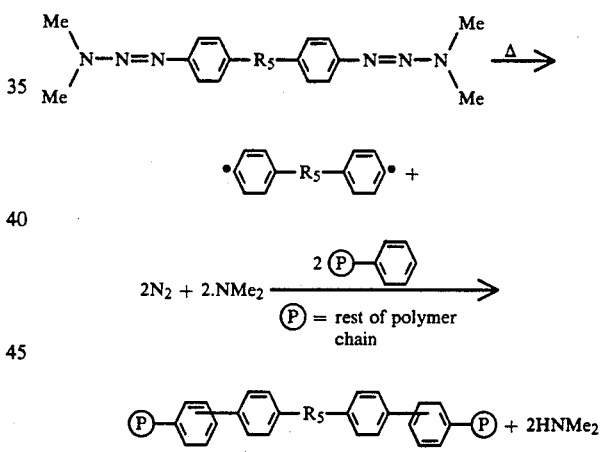

As a matter of convenience, in the equations the triazene groups have been depicted as decomposing simultaneously to give a diradical. It is possible, if not likely, that the decomposition is not entirely simultaneous, so that monoradicals are also formed, which, however, would react in a similar fashion, albeit sequentially. A noteworthy aspect is that the crosslinks are via aryl-aryl bonds. Compared to their aliphatic counterparts, these are much less vulnerable to thermooxidative or other chemical attack and hence stabler.

The following —R$_5$— groups are preferred, because the corresponding bistriazenes have relatively high molecular weights compared to bistriazenes having a lesser number of aromatic rings and they (or the radicals formed therefrom) are less likely to escape from the mixture with the polymer as the mixture is heated to crosslink it:

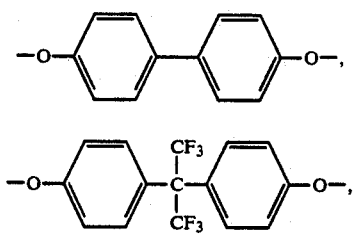

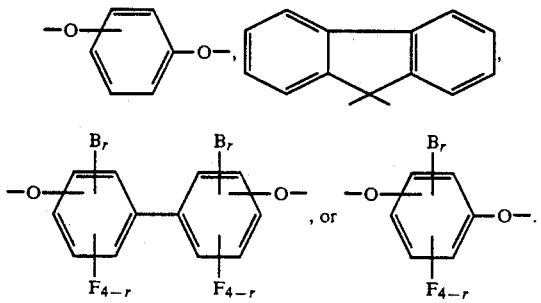

These —$R_5$— groups are also preferred because they do not have backbone C—H groups which would be susceptible to thermo-oxidative degradation, do not possess polar groups (to avoid increasing the dielectric constant or moisture uptake of the crosslinked polymer), and do not possess ester, azo, amide, and other similar groups which are subject to hydrolytic or other forms of degradation. In the known uses for bistriazene compounds such as intermediates for making dyes (Mueller et al., in U.S. Pat. No. 3,555,004 (1971)) and herbicides (Mazza et al., Farmaco Ed. Sc. 29 (1), 58 (1974)), the above considerations do not come into play, and consequently the bistriazenes specifically disclosed in the prior art do not possess these features.

Particularly preferred bistriazene compounds are

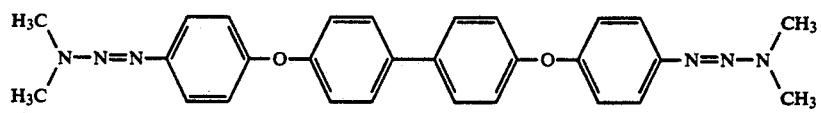

and

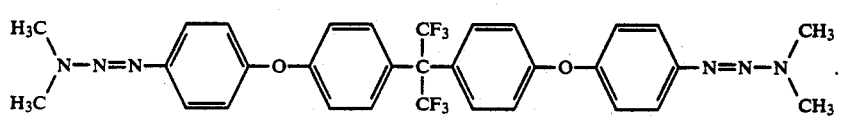

Aromatic polymers which can be crosslinked by our bistriazene compounds include poly(imides), poly(aryl ether ketones), poly(aryl ether sulfones), poly(quinolines), poly(quinoxalines), and fluorinated poly(naphthyl ethers).

Suitable poly(imides) include those comprising repeat units Ia–Id. Poly(imide) Ib is available from Ethyl Corporation under the tradename Eymyd HP-40. Poly(imide) Ic is available from Hoechst under the tradename Sixef-44. Poly(imides) such as Id are sometimes called "poly(ether imides)," because their repeat units contain both ether and imide groups. Poly(imide) Id is available from General Electric under the tradename Ultem. Poly(imides) such as Ie are sometimes called "poly(ether ketone imides)," because their repeat units contain ether, ketone, and imide groups. The preparation of poly(ether ketone imides) is disclosed in Dahl et al., U.S. Pat. No. 4,868,271 (1989). As used herein, the term "poly(imide)" includes "poly(ether imide)" and "poly(ether ketone imides)".

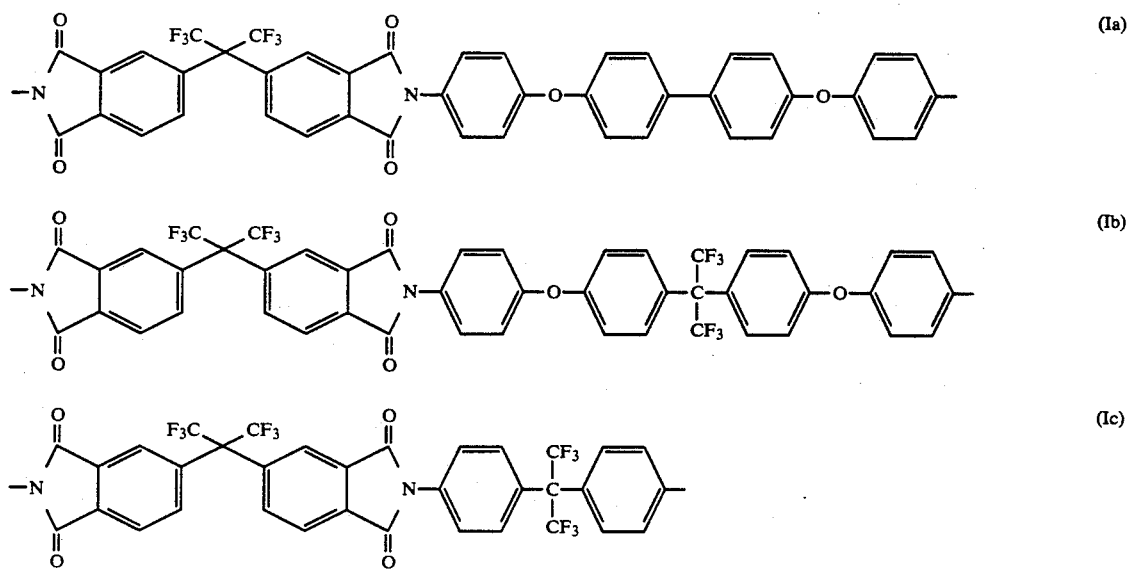

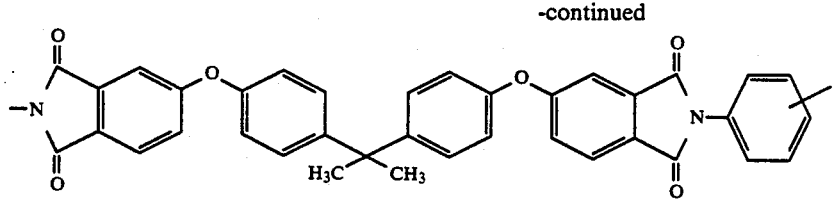

(Id)

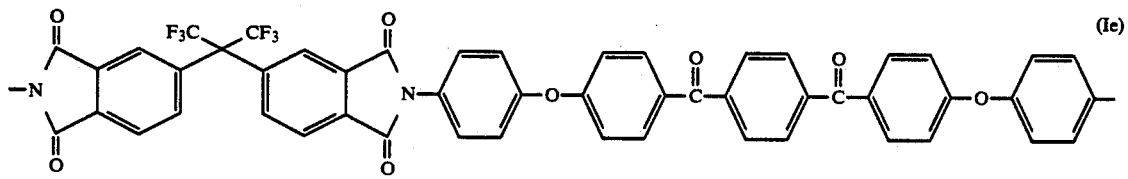

(Ie)

Poly(aryl ether ketones) which can be crosslinked by our bistriazene compounds include those comprising repeat units IIa–IIf. Poly(aryl ether ketone) IIf is available from ICI under the tradename PEEK. A preferred method for the preparation of poly(aryl ether ketones) is disclosed in Jansons et al., U.S. Pat. No. 4,709,007 (1987).

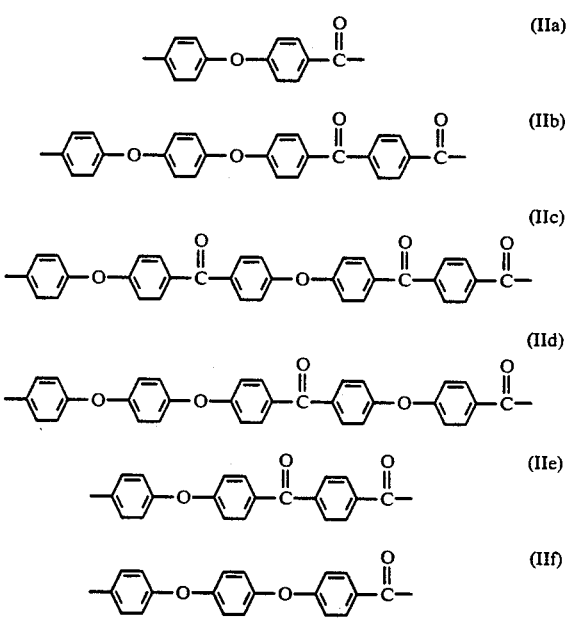

(IIa)
(IIb)
(IIc)
(IId)
(IIe)
(IIf)

Poly(aryl ether sulfones) which can be crosslinked according to our invention include those comprising repeat units IIIa–IIIb. Sometimes poly(aryl ether sulfone) IIIa and IIIb are distinguished in the art by calling the former "poly(ether sulfone)" and the latter simply "poly(sulfone)." However, such nomenclature is somewhat inapt, as IIIb clearly also possesses ether groups. As used herein, the term "poly(aryl ether sulfone)" includes IIIa, IIIb and other aromatic polymers having both ether and sulfone backbone groups.

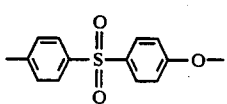

(IIIa)

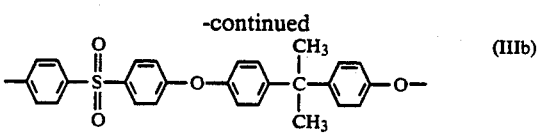

(IIIb)

Poly(quinolines) which can be crosslinked according to our invention include those having repeat unit IV:

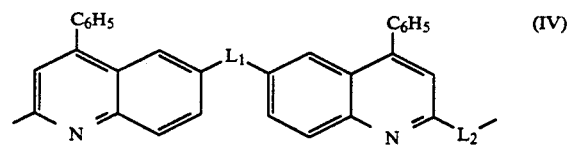

(IV)

wherein —$L_1$— is a direct bond or —O— and —$L_2$— is —$C_6H_5$, —$C_6H_4C_6H_4$—, —$C_6H_4OC_6H_4$—, or a fluorinated divalent moiety. Polyquinoline in which $L_2$ is a fluorinated divalent moiety is especially preferred for electronic insulator applications because of its low dielectric constant (2.7 at 10 KHz), which changes very little in going from a dry environment (0% relative humidity (% RH)) to a humid one (60% RH). The preparation of poly(quinolines) which can be crosslinked by our bistriazenes is described in Stille, Macromolecules 14,870 (1981) and in Norris et al., Macromolecules 9,496 (1976).

Poly(quinoxalines) which can be crosslinked with bistriazenes include those comprising repeat unit V:

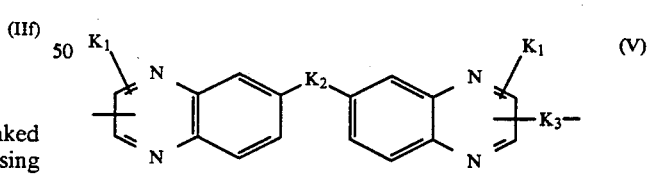

(V)

where —$K_1$ is —H or —$C_6H_5$; —$K_2$— is a direct bond, —O—, —S—, —$SO_2$—, —CO—, or —$C_6H_4$—; and —$K_3$ is —$C_6H_5$, —$C_6H_4C_6H_4$—, —$C_6H_4OC_6H_4$—, —$C_6H_4SO_2C_6H_4$—, or —$C_6H_4C(CF_3)_2C_6H_4$—. Poly(quinoxalines) are especially useful as insulators in microelectronic devices and components. The preparation of poly(quinoxalines) and their use in microelectronic applications is described by Labadie et al., SAMPE J. 25(6), 18 (1989) and Hergenrother, J. Macromol. Sci. Rev. Macromol. Sci., C6(1), 1 (1971).

The aforementioned polymers may be homopolymers consisting essentially of the specified repeat units or copolymers in combination with other repeat units.

Our invention can also be used to crosslink nonaromatic fluoropolymers which have aliphatic C—H groups, i.e., are not perfluorinated. The fluorpolymers can be either thermoplastic or elastomeric. The C—H groups act as insertion sites for the phenyl radicals generated from the bistriazene compounds Suitable thermoplastic fluoropolymers include poly(vinylidene fluoride) (—$CH_2CF_2$—), available from Pennwalt under the tradename Kynar; ethylene-tetrafluoroethylene copolymer or ETEE (—$CH_2CH_2$—$CF_2CF_2$—), available from Du Pont under the tradename Tefzel; poly(vinyl fluoride) (—$CH_2CHF$—), available from Du Pont under the tradename Tedlar; and tetrafluoroethylene-hexafluoroisobutylene copolymer, available from Ausimont under the tradename CM-X. Suitable elastomeric fluoropolymers include vinylidene fluoride-hexafluoropropylene copolymer, available from Du Pont under the tradename Viton A; vinylidene fluoride-hexafluoropropylene-tetrafluoroethylene copolymer, available from Du Pont under the tradename Viton B; vinylidene fluoride-tetrafluoroethylene-perfluoro(methyl vinyl ether) copolymer, available from Du Pont under the tradename Viton GLT; and tetrafluoroethylene-propylene copolymer, available from Asahi under the tradename Aflas.

A preferred crosslinking method is to dissolve the polymer is an appropriate solvent, such as N,N-dimethylacetamide (DMAc) or N-methylpyrrolidone (NMP) together with the desired amount of bistriazene compound, typically at a concentration of between about 20 and about 30 weight % solids. For poly(aryl ether ketones), the preferred solvent system is a 1:1 (v/v) mixture of dichloromethane and 1,1,1,3,3,3-hexafluoro-2-propanol or of dichloromethane and trifluoroacetic acid. The amount of bistriazene compound should be an amount effective to crosslink the polymer, which may vary somewhat from polymer to polymer but may be readily determined empirically. The amount of bistriazene compound is preferably between about 10 and about 40, more preferably between about 15 and about 30 weight %, based on the combined weights of polymer and bistriazene compound. A thin film of polymer is then deposited on a substrate by spin coating. The solvent is driven off by a "soft baking" procedure at a relatively low temperature (typically about 100°–200° C.), below that required to trigger the crosslinking reaction. Then, the polymer is crosslinked (cured) by heating to a higher temperature, between about 300° and about 450° C., preferably between about 350° and about 400° C. Typical curing times are about 15 to about 90 min. Longer curing times may be employed, but generally no advantage is derived therefrom. It is to be understood that complex or staged cure cycles, for example X minutes at temperature A followed by Y minutes at temperature B, may be employed.

As an alternative to solvent mixing methods, melt mixing by conventional techniques, such as with a two-roll mill, a Brabender or Banbury internal mixer, or a twin-screw extruder, can be used.

The bistriazene compounds of our invention have exceptional stability up to moderately elevated temperatures, so that stock coating solutions or mixtures of the polymer and the bistriazene compound can be stored for long times without premature crosslinking. The bistriazene compounds mostly are stable up to at least 250° C., as determined by differential scanning calorimetry (DSC).

In another embodiment, crosslinking can be effected by the acid catalyzed decomposition of the bistriazene. For example, when casting a film of poly(aryl ether ketone)-bistriazene mixture from dichloromethane-trifluoroacetic acid, a freshly prepared solution should be used, because trifluoroacetic will catalyze the reaction.

Crosslinking of polymers improves their solvent resistance and can convert a material from one which stress-crazes (or is otherwise attacked) when exposed to a particular solvent to one which does not. Consequently, polymers crosslinked according to our invention can be used in environments in which the corresponding uncrosslinked polymer cannot be used. Generally, crosslinking to at least 80% gel content is desirable to ensure craze resistance. Polymers so crosslinked are particularly useful in a multilayered integrated circuit article. The article comprises a substrate, for example, silicon, glass or ceramic, with at least one layer of crosslinked polymer deposited on a surface thereof. Generally a plurality of layers are successively deposited and cured. One of more layers of conductive material can be interposed between two adjacent layers of cured polymer. The conductive layer(s) normally are not coextensive with the polymer layers, but instead form a plurality of electrically conductive pathways. The conductive layer(s) are preferably metallic, but can comprise a semiconductive material.

A multilayer article may be prepared by spin coating a solution of polymer and bistriazene compound onto the substrate. The solvent is evaporated and the polymer is cured at an elevated temperature. Typically the coating thickness is about 5 to about 40 microns. A conductive layer having electrical pathways of the desired pattern is applied over the polymer layer, using for example a sputtering technique with the appropriate areas masked to create the desired conductive pathways. The next polymer layer is then applied in the same manner as the previous one. These steps can be repeated until the desired multi-layer article is produced. The multilayered article can be used as a packaging-interconnect device for integrated circuits.

The performance of a multilayer integrated circuit article is sensitive to small changes in the dielectric constant of the interlayer insulating material. It is preferred to have an insulating material with as low a dielectric constant as possible, preferably about or less than 3.0. A lower dielectric dielectric constant permits the article to operate with higher circuit densities, lesser pulse broadening, and higher signal propagation speed. This factor is particularly important in the case of poly(imide) interlayer insulating material. Poly(imides) absorb water in moist environments, resulting in an increase in their dielectric constant. Thus, a poly(imide) insulated multilayer article which performs satisfactorily in a dry air environment may perform unsatisfactorily in a humid environment. The effect of insulator dielectric constant on multilayer integrated circuits is discussed in "Microelectronics Packaging Handbook," Tummala et al (eds.), pp. 687–692 (van Nostrand Reinhold 1989); Watari et al., U.S. Pat. No. 4,744,007 (1988); and Budde et al., U.S. Pat. No. 4,732,843 (1988). Further, some crosslinking agents may cause an increase in the dielectric constant of the base polymer. Our bistriazene crosslinking agents are advantageous in that they do not significantly increase the dielectric constants of the polymers being crosslinked.

The practice of our invention may be further understood by reference to the following examples, which are provided by means of illustration, not limitation.

EXAMPLE 1

This example describes a general procedure for the preparation of bistriazene compounds of our invention. Bistriazenes A-I in Table I below were prepared by this procedure.

A solution of diamine (40 mmol)

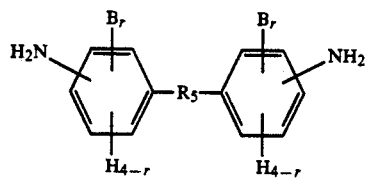

where $-R_5-$, $R_6$, and r are as previously defined, was prepared, with tetrahydrofuran (THF, 400 mL) as the solvent. (Methanol was used in the case of bistriazene B.) The solution was transferred into a 1-liter, 3-neck round bottom flask equipped with a mechanical stirrer, thermometer, and addition funnel. A solution of 12N hydrochloric acid (24 mL, 288 mmol) in water (300 mL) was poured in slowly, with vigorous stirring. After 5 min, the contents of the flask were chilled to $-5°$ C. with continued stirring. A solution of sodium nitrite (11.0 g, 159.4 mmol) in ice-water (150 mL) was added to the chilled contents over a period of 30 min through the addition funnel. Stirring was continued for an additional 60 min, maintaining the temperature below 0° C. At the end of this period, the THF was removed under reduced pressure at 25° C. The remaining aqueous material was cooled to 0° C. and neutralized to pH 6-7 with saturated sodium carbonate solution. The neutralized solution was immediately poured into a 2-liter beaker containing a freshly prepared solution of dimethylamine hydrochloride (16.3 g, 200 mmol) (for bistriazenes H and I, diethylamine and aniline were used, respectively) and sodium carbonate (33.9 g, 320 mmol) in ice-water (450 mL). The mixture was stirred vigorously with a mechanical stirrer for 20 min and then extracted with dichloromethane (4×80 mL). The combined extracts were dried over anhydrous magnesium sulfate and decolorized with activated charcoal. The dichloromethane was removed under reduced pressure at 35° C. The residue was recrystallized from dichloromethane-acetone (1/5 v/v). The yields, melting points, and decomposition temperatures of various bistriazenes are provided in Table I. Table II provides their spectral characteristics.

TABLE I

Yield, Melting Point, and Decomposition Temperature of Bistriazene Compounds $$R_1R_2N-N=N-C_6H_4-R_5-C_6H_4-N=N-NR_3R_4$$

| Ref. | $-R_5-$ | $R_1-R_4$ | Yield (%)* | M.p. (°C.) | $T_d$ (°C.) |
|---|---|---|---|---|---|
| A | $-O-$ | $R_1-R_4 =$ Me | 58.6 | 53-5 | 268.5 |
| B | $-SO_2-$ | $R_1-R_4 =$ Me | 48.4 | 209-11 | 290.3 |
| C | $-O-C_6H_4-O-$ | $R_1-R_4 =$ Me | 91.2 | 140-43 | 277.0 |
| D | $-O-C_6H_4-C_6H_4-O-$ | $R_1-R_4 =$ Me | 76.5 | 167-69 | 263.0 |
| E | $-O-C_6H_4-SO_2-C_6H_4-O-$ | $R_1-R_4 =$ Me | 56.8 | 159-60 | 288.8 |
| F | $-O-C_6H_4-C(CH_3)_2-C_6H_4-O-$ | $R_1-R_4 =$ Me | 62.6 | 74-6 | 279.4 |
| G | $-O-C_6H_4-C(CF_3)_2-C_6H_4-O-$ | $R_1-R_4 =$ Me | 68.0 | 125-28 | 282.8 |
| H | $-O-C_6H_4-C_6H_4-O-$ | $R_1-R_4 =$ Et | 67 | 105-8 | 350 |

TABLE I-continued
Yield, Melting Point, and Decomposition Temperature of Bistriazene Compounds

| Ref. | —R₅— | R₁–R₄ | Yield (%)* | M.p. (°C.) | $T_d$ (°C.) |
|---|---|---|---|---|---|
| I | —O—⟨⟩—⟨⟩—O— | R₁, R₄ = H; R₂, R₄ = Ph | 61 | 155–57 | 180 |

*Yield not optimized
**Decomposition temperature measured by DSC (10° C./min)

TABLE II
Spectral Characteristics of Bistriazene Compounds

| Ref. (*) | ¹H-NMR (CDCl₃)** δ (ppm) | Assignment | IR (KBr) cm⁻¹ | Assignment |
|---|---|---|---|---|
| A | 3.30 (s, 12H) | —N-CH₃ | 1585 (w) | conj. C=C |
|  | 6.91–7.60 (m, 8H) | Ar—H | 1492 (s) | N=N |
|  |  |  | 1231 (s) | C—O—C |
|  |  |  | 1083 (s) | C—N |
| B | 3.32 (s, 12H) | —N-CH₃ | 1476 (w) | N=N |
|  | 7.40–8.10 (m, 8H) | Ar—H | 1289 (s) | O=S=O |
|  |  |  | 1148 (s) | O—S—O |
|  |  |  | 1108 (s) | C—N |
| C | 3.29 (s, 12H) | —N-CH₃ | 1448 (s) | N=N |
|  | 6.82–7.48 (m, 8H) | Ar—H | 1222 (s) | C—O—C |
|  |  |  | 1084 (s) | C—N |
| D | 3.32 (s, 12H) | —N-CH₃ | 1492 (s) | N=N |
|  | 6.86–7.66 (m, 8H) | Ar—H | 1250 (s) | C—O—C |
|  |  |  | 1076 (s) | C—N |
| E | 3.29 (s, 12H) | —N-CH₃ | 1486 (s) | N=N |
|  | 6.81–8.02 (m, 8H) | Ar—H | 1295 (m) | O—S—O |
|  |  |  | 1189 (s) | O=S=O |
|  |  |  | 1239 (s) | C—O—C |
|  |  |  | 1104 (s) | C—N |
| F | 1.61 (s, 6H) | —C—CH₃ | 1493 (m) | N=N |
|  | 3.29 (s, 12H) | —N-CH₃ | 1246 (s) | C—O—C |
|  | 6.72–7.53 (m, 16H) | Ar—H | 1247 (s) | C—O—C |
|  |  |  | 1198 (s) | C—F |
|  |  |  | 1086 (s) | C—N |
| H | 1.43 (t, 12H) | CH₃ | 1600 | conj. C=C |
|  | 3.90 (q, 8H) | N-CH₃ | 1495 | N=N |
|  | 6.90–7.89 (m, 16H) | Ar-H | 1240 | C—O—C |
|  |  |  | 1087 | C—N |
| I | 6.87–7.63 (m) | Ar—H | 3296 (w) | s-amine |
|  |  |  | ~3035 (w) | Ar—H |
|  |  |  | 1599 (m) | conj. C=C |
|  |  |  | 1500 (s) | N=N |
|  |  |  | 1246 (s) | C—O—C |
|  |  |  | 1100 (s) | C—N |

*See TABLE I
**Acetone-d₆ for compound H; DMSO-d₆ for compound I

EXAMPLE 2

This example describes the general procedure for the preparation of bistriazene-crosslinked polymer films by a spin coating technique. The polymer is dissolved in a solvent such as DMAc or NMP, with stirring and heating. The bistriazene compound in the desired amount is added to the still-warm polymer solution. The mixture is stirred until all the solids are dissolved. The resulting formulation is filtered through a layer of packed glass wool (other filtering media can be used) and degassed under reduced pressure. A typical formulation contains 20–30 weight % solid content.

A thin film of crosslinked polymer can be obtained by spin-casting the formulation onto a 4×4 in (ca. 10×10 cm) glass plate. The coated plate is first "soft baked" for 30 min each at 100° C. and 200° C. to drive off the solvent. The film is then cured at 400° C. for 30 min. A free-standing film can be obtained by peeling off the polymer film after 4–16 hr soaking in 90° C. water. A typical film is 5–50 μ thick.

Alternatively, a thick disc of crosslinked polymer (0.5 to 3 mm thick) can be obtained by transferring an aliquot of the above formulation (approximately 2–5 g) to an aluminum weighing pan and soft-baking for 16 hr at 100° C. and then 2 hr at 200° C., followed by curing at 400° C. for 60 min. Some bubbling and void formation is observed in the thick discs, presumably due to the evolution of nitrogen and amine. This effect can be reduced by curing at a slightly lower temperature, about 300° to about 350° C.

EXAMPLE 3

In this example, the effect of bistriazene crosslinking agents on the dielectric constant of poly(imides) used in multilayer integrated circuit articles is compared against the effect of a prior art crosslinking agent. The bistriazene crosslinking agents were D and G (see Table I).

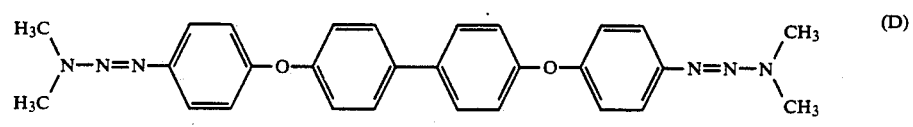

(D)

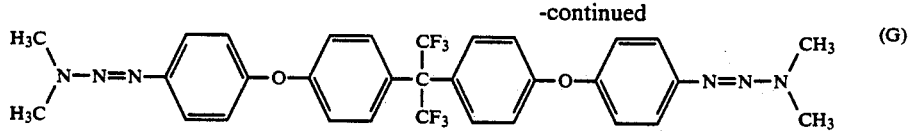

The prior art crosslinking agent was acetylene terminated oligomer VI, available from National Starch under the tradename Thermid:

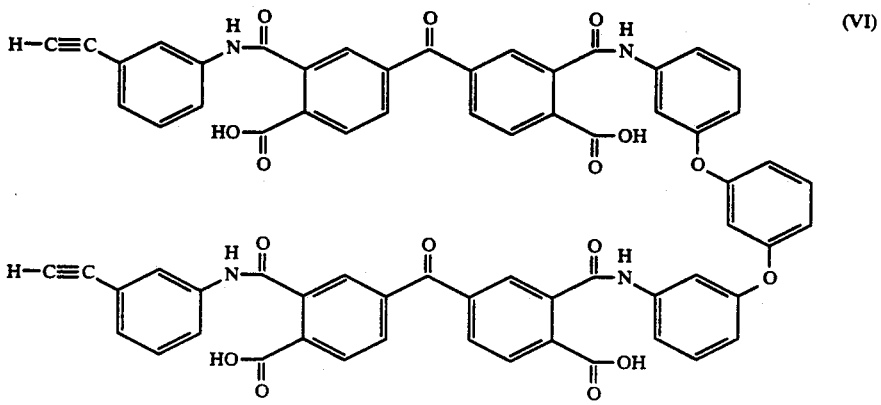

The poly(imides) crosslinked were Ia and Ib. Results are presented in Table III. It can be seen from Table III that the increase in dielectric constant in going from a dry (0% RH) environment to a humid one (60% RH) is much lesser in the case of bistriazene crosslinking agents D and G. (The uncrosslinked polymer would be an unsuitable insulator, despite its small change in dielectric constant, because it would lack the necessary solvent resistance.)

TABLE III

| | Effect of Crosslinking Agent on Dielectric Constant of Poly(imides) | | | |
|---|---|---|---|---|
| Poly(imide) | Crosslinking Agent** | Dielectric Constant* | | |
| | | at 0% RH | at 60% RH | % Change |
| Ia | None | 2.84 | 3.21 | 13.05 |
| | Thermid | 2.97 | 3.57 | 20.25 |
| | Bistriazene D | 2.82 | 3.30 | 16.90 |
| | Bistriazene G | 2.84 | 3.21 | 13.18 |
| Ib | None | 2.72 | 3.03 | 11.64 |
| | Thermid | 2.82 | 3.22 | 14.42 |
| | Bistriazene D | 2.80 | 3.11 | 11.01 |
| | Bistriazene G | 2.75 | 3.07 | 11.54 |

*Measured at 10 KHz
**20 wt % crosslinking agent; crosslinked by heating 30 min/100° C., 30 min/200° C., then 30 min/400° C.

EXAMPLE 4

This example demonstrates the crosslinking of poly(imide) Ia by various bistriazene compounds. Films of poly(imide) Ia containing 20 wt % bistriazene compound were crosslinked by heating 30 min each at 100°, 200°, and 400° C. The results are presented in Table IV. The extent of crosslinking was estimated by means of gel content. The gel content was defined as the percent ratio of the weight of a given polymer sample after extraction compared to its weight before extraction. The extraction conditions were: 24 or 48 hr continuous extraction with boiling NMP in a Soxhlet apparatus under nitrogen. (In the case of poly(aryl ether ketones), extraction was done with concentrated sulfuric acid at about 150° C.) Prior to extraction thin film (5–50μ) polymer samples were cut into small pieces no larger than 3×3 mm. Thick disk polymer samples (1–3 mm thick) were broken down into small pieces no larger than 1 mm² in size before extraction. After extraction, residual polymer samples were dried under vacuum (0.5 mm) at 150° C. overnight before weighing.

TABLE IV

| Crosslinking of Poly(imide) Ia by Bistriazene Compounds | |
|---|---|
| Bistriazene* | Gel Content (%) |
| A | 0 |
| B | 65.1 |
| C | 54.8 |
| D | 85.1 |
| E | 20.5 |
| F | 16.2 |
| G | 55.1 |

*See Table I

EXAMPLE 5

This example studies the effect of curing time, curing temperature, and amount of bistriazene D on the solvent induced craze resistance of poly(imides) Ia and Ib. Thin films 10–20μ thick) of polymer-bistriazene compositions were prepared by spin casting onto a 4×4 inch glass plate. This thin film was soft baked for 30 min at 100° C. and then for 30 min at 200° C. before curing. A second film of the same formulation was then cast on top of the cured first film, in a manner such that the second film covered no more than one half the area of the first film. The coated plate was then soft baked and cured again. During the second soft baking cycle, solvent from the second film penetrates and swells up the first film. If the first film was not sufficiently crosslinked, it would stress craze after the solvent was driven off during the second heating cycle. Crazing could be easily detected under a light microscope.

The results provided in Table V show that, as the concentration of bistriazene D is increased, a lesser cure time and/or a lower cure temperature is required to impart solvent induced craze resistance to the poly(imides). Conversely, as the cure time and/or temperature is increased, the amount of bistriazene D required is reduced.

TABLE V

Effect of curing time and temperature
and concentration of bistriazene D

on solvent stress crazing of poly(imides)

| Poly(imides) | Curing Temp. (°C.) | Weight % D | Crazing after curing for | | |
|---|---|---|---|---|---|
| | | | 15 min | 30 min | 45 min |
| Ia | 300 | 10 | Yes | Yes | Yes |
| | | 15 | Yes | Yes | Yes |
| | | 20 | Yes | Yes | Yes |
| | 350 | 10 | Yes | Yes | Yes |
| | | 15 | Yes | Yes | No |
| | | 20 | Yes | No | No |
| | 400 | 10 | Yes | No | No |
| | | 15 | No | No | No |
| | | 20 | No | No | No |
| Ib | 400 | 10 | Yes | Yes | — |
| | | 15 | Yes | Yes | — |
| | | 20 | Yes | Yes | — |
| | | 25 | Yes | Yes | — |
| | | 30 | No | No | — |
| | | 40 | No | No | — |
| | 430 | 20 | Yes | Yes | — |
| | | 30 | No | No | — |
| | | 40 | No | No | — |
| | 450 | 20 | Yes | No | — |
| | | 30 | No | No | — |
| | | 40 | No | No | — |

EXAMPLE 6

In this example, the ability of bistriazene D to crosslink various different types of polymers is demonstrated. The results are provided in Table VI, showing effective crosslinking a wide variety of different polymers.

TABLE VI

Crosslinking of various polymers by bistriazene D

| Polymer | Wt. % Bistriazene D | % Gel |
|---|---|---|
| Poly(imide) Ia | 20 | 93 |
| Poly(imide) Ib | 20 | 81 |
| Poly(imide) Ic | 20 | 1 |
| Poly(imide) Id | 20 | 83 |
| Poly(imide) Ie | 30 | 57 |
| Poly(aryl ether ketone) IIa | 10 | 64 |
| Poly(aryl ether sulfone) IIIa | 15 | 98 |
| Poly(quinoline) V (—L$_2$— = fluorinated divalent moiety) | 20 | 92 |
| Poly(vinylidene fluoride) | 20 | 77 |

*Polymer disk (1-3 mm) used for gel content determination. Disc of polymer and bistriazene D heated according to this schedule: 16 hr/100° C., 60 min/200° C., 60 min/400° C.

EXAMPLE 7

This example describes the preparation of another bistriazene crosslinking agent of this invention, having the structure

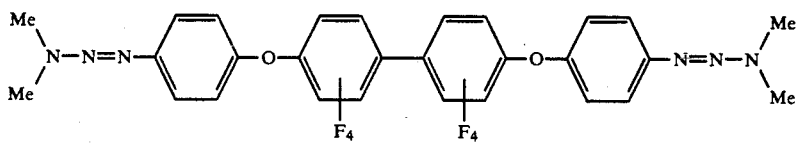

To a solution of 8 g (15.6 mmol) of 4,4'-bis(4-aminophenoxy)decafluorobiphenyl in 160 mL of THF in a 500 mL three-neck flask equipped with a mechanical stirrer, a thermometer, and an addition funnel, solution of 9.1 mL (109.2 mmol) 12N hydrochloric acid in 80 mL of water was added slowly. The resulting mixture was chilled to −5° C. with constant stirring. A solution of 4.32 g (62.4 mmol) sodium nitrite in 50 mL of ice water was added to this chilled mixture dropwise over a period of 30 min with vigorous stirring. During the addition, the temperature of the reaction mixture did not exceed −3° C. After the addition, the reaction mixture was stirred below 0° C. for an additional 60 min. At the end of the reaction, the organic solvent was removed under reduced pressure at 25° C. The resulting aqueous solution was chilled to 0° C. and neutralized to pH 6-7 with a saturated solution of sodium carbonate. The neutralized solution was immediately poured into a 1 L beaker containing a freshly prepared solution of 6.37 g of dimethylamine hydrochloride and 13.24 g of sodium carbonate in 150 mL of water with vigorous stirring. After an additional 10 minutes of stirring, the reaction mixture was extracted with four 50 mL portions of dichloromethane. The combined extracts were washed with two 50 mL portions of water, dried over anhydrous magnesium sulfate, and decolorized with activated charcoal. The solvent was then removed under reduced pressure at 35° C. and the residue redissolved in the minimum amount of acetone. To the acetone solution was added 100 mL of pentane with stirring. The precipitate was filtered, washed with more pentane, and vacuum dried to yield 5.96 g (61.2%) of bistriazene, mp 133°-35° C.

EXAMPLE 8

A bistriazene having the structure

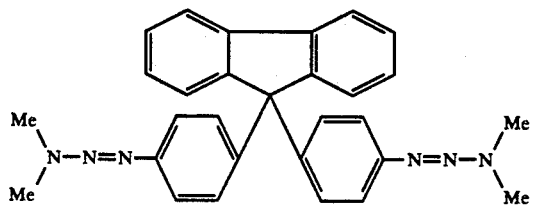

was prepared following the procedure and stoichiometric ratios of Example 7, using 5.44 g (15.6 mmol) of 9,9-bis(4-aminophenyl)fluorene. The yield was 5.50 g (76.6%), mp 197°-99° C.

EXAMPLE 9

A bistriazene having the structure

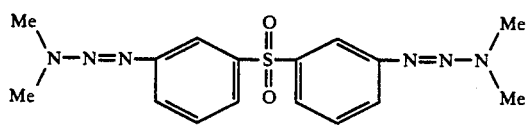

was prepared following the procedure and stoichiometric ratios of Example 7, except as noted below, using 7.75 g (31.2 mmol) of 3-aminophenyl sulfone which had been purified by decolorization with activated charcoal and recrystallization from THF. After the dichloromethane extraction step, the solvent was evaporated and the residue was redissolved in the minimum of acetone. To the acetone solution was added 100 mL of methanol, with stirring. The precipitate was filtered, washed with methanol, air dried, and then vacuum dried to yield 5.16 g (45.7%) of bistriazene, mp 120°-25° C.

What is claimed is:

1. A bistriazene compound of the formula

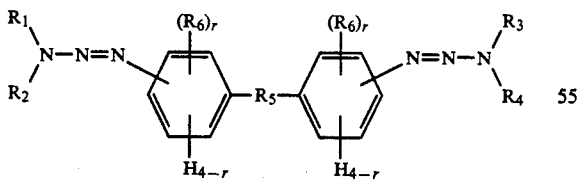

wherein —$R_1$, —$R_2$, —$R_3$, and —$R_4$ are independently —H, —$C_6H_5$, —$C_6H_5$, —$C_6H_4Y$, or $C_1$-$C_4$ alkyl; —$R_5$— is

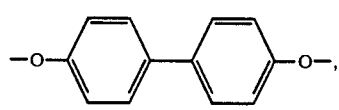

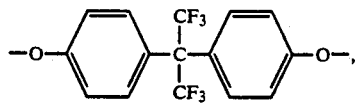

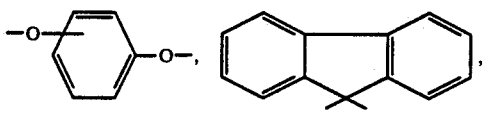

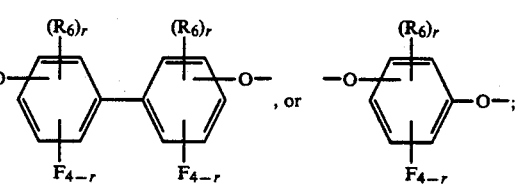

—$R_6$ is —F, —Cl, —Br, —$CH_3$, or —$CF_3$; r is 0, 1, 2, 3, or 4; and —Y is halogen, —$NO_2$, —$C_6H_5$, or $C_1$-$C_4$ alkyl.

2. A bistriazene compound according to claim 1, wherein each of —$R_1$, —$R_2$, —$R_3$ and —$R_4$ is methyl and r is 0.

3. A bistriazene compound according to claim 1, wherein —$R_5$— is

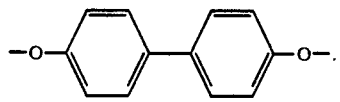

4. A bistriazene compound according to claim 1, wherein —$R_5$— is

5. A bistriazene compound according to claim 1, wherein —$R_5$— is

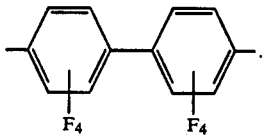

6. A bistriazene compound according to claim 1, wherein —$R_5$— is

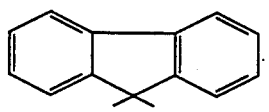

7. A bistriazene compound according to claim 1, having the formula

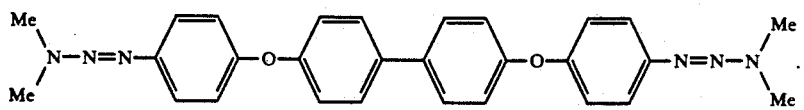
8. A bistriazene compound according to claim 1, having the formula
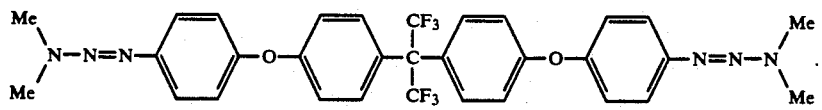
9. A bistriazene compound according to claim 1, having the formula
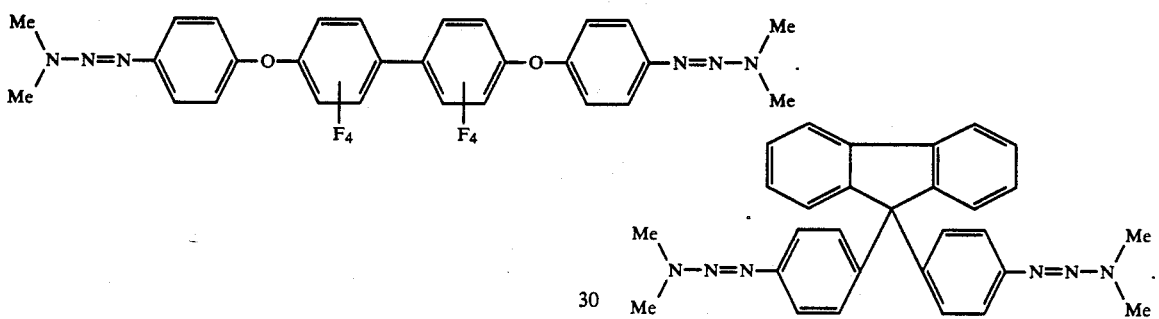
10. A bistriazene compound according to claim 1, having the formula
* * * * *